(12) United States Patent
Vogele

(10) Patent No.: US 11,020,201 B2
(45) Date of Patent: Jun. 1, 2021

(54) DEVICE FOR ATTACHING MEDICAL TARGET DEVICES AND THE LIKE

(71) Applicants: ISYS MEDIZINTECHNIK GMBH, Kitzbühel (AT); Michael Vogele, Schwabmünchen (DE)

(72) Inventor: Michael Vogele, Schwabmünchen (DE)

(73) Assignee: ISYS MEDIZINTECHNIK GMBH, Kitzbuhel (AT)

( * ) Notice: Subject to any disclaimer, the term of this patent is extended or adjusted under 35 U.S.C. 154(b) by 657 days.

(21) Appl. No.: 14/916,491

(22) PCT Filed: Sep. 4, 2014

(86) PCT No.: PCT/EP2014/002399
§ 371 (c)(1),
(2) Date: Jul. 11, 2016

(87) PCT Pub. No.: WO2015/032498
PCT Pub. Date: Mar. 12, 2015

(65) Prior Publication Data
US 2016/0317240 A1    Nov. 3, 2016

(30) Foreign Application Priority Data

Sep. 4, 2013 (DE) .......................... 202013007831.6

(51) Int. Cl.
*A61B 90/11* (2016.01)
*A61B 17/00* (2006.01)
(Continued)

(52) U.S. Cl.
CPC ........ *A61B 90/11* (2016.02); *A61B 17/00234* (2013.01); *A61B 17/3403* (2013.01);
(Continued)

(58) Field of Classification Search
CPC .... A61B 2017/0056; A61B 2017/3407; A61B 2017/3409; A61B 5/6865; A61B 17/3423;
(Continued)

(56) References Cited

U.S. PATENT DOCUMENTS 3,457,922 A    7/1969  Ray
7,881,823 B2   2/2011  Demathelin et al.
(Continued)

OTHER PUBLICATIONS

International Search Reported dated Dec. 16, 2014, in corresponding International Application No. PCT/EP2014/002399.

*Primary Examiner* — Sarah W Aleman
(74) *Attorney, Agent, or Firm* — Venable LLP; Michele V. Frank

(57) ABSTRACT

The aim of the invention is to create a device for arranging medical targeting devices, markers, probes or surgical instruments for image-assisted, minimally invasive operations, which has a simple construction and is easy to use. Said device according to the invention has at least one carrier element (1) that can be positioned preferably with an adhesive layer on the surface of the body, and a fine-positioning unit (2). It is proposed that the carrier element (1) comprises at least one interlocking mount (3) for the fine-positioning unit (2) which has a matching complementary shape (3*c*).

12 Claims, 3 Drawing Sheets

(51) Int. Cl.
    *A61B 17/34*         (2006.01)
    *A61B 90/18*         (2016.01)
    *A61B 90/00*         (2016.01)

(52) U.S. Cl.
    CPC .............. *A61B 90/18* (2016.02); *A61B 90/39* (2016.02); *A61B 2017/00566* (2013.01); *A61B 2017/3407* (2013.01); *A61B 2090/3983* (2016.02)

(58) Field of Classification Search
    CPc ......... A61B 90/11; A61B 46/23; A61B 17/34; A61B 1/313; A61B 1/3135; A61B 2017/3419; A61B 10/02; A61B 2017/348; A61M 25/02
    See application file for complete search history.

(56) References Cited

U.S. PATENT DOCUMENTS

| | | |
|---|---|---|
| 2002/0133174 A1 | 9/2002 | Charles et al. |
| 2003/0125753 A1 | 7/2003 | Saracione |
| 2006/0100501 A1* | 5/2006 | Berkelman ........ A61B 17/3403 600/415 |
| 2007/0276407 A1 | 11/2007 | Vogele |
| 2009/0069945 A1 | 3/2009 | Burgkart |
| 2010/0137680 A1* | 6/2010 | Nishikawa ........... B25J 17/0216 600/102 |
| 2012/0022368 A1* | 1/2012 | Brabrand ............... A61B 90/11 600/427 |
| 2012/0184956 A1 | 7/2012 | Velusamy et al. |
| 2012/0266898 A1 | 10/2012 | Vogele |

\* cited by examiner

DEVICE FOR ATTACHING MEDICAL TARGET DEVICES AND THE LIKE

The invention relates to a device for attaching medical target devices and the like according to the pre-characterizing features of claim 1.

"Attachment" is to be understood as the positioning of medical instruments, in particular medical target devices, markers, probes and/or surgical instruments to be adjusted and reliably fixed in image-guided, minimally invasive surgical procedures.

In many areas of human medicine or medical research a secure fixing or (mechanical) installation of equipment or appliances is required. This is in particular of great importance in the field of diagnostic and therapeutic radiology and/or oncology, radiotherapy or operative/surgical procedures (neurosurgery, ENT, orthopedics, etc.).

The inclusion of computer technology in diagnosis and therapy increases the demands on accuracy and repeatability both in fixing a stereotactic frame system at humans and in the fixation of the human body itself. Comfort, speed of application, mobility and costs play a significant role. In addition to the conventional fixation types on the body with straps or sleeves or even by screwing in the bone, formworks are also known which, however, show several disadvantages, in particular with regard to the fixation accuracy. Other techniques such as rails, thermoplastic material, plastic forms, plaster, etc. have similar disadvantages. In addition, these methods are still associated with considerable financial and time expenditure and are therefore only used for long-term applications. In DE 20 2011 005 573, Applicant has already proposed a molding element, which substantially avoids the above disadvantages.

Thus, the invention is based on the object to provide a device for attachment of medical target devices which are easy in design and application and patient-friendly to a high degree. Moreover the device should allow the exact placement of calibration points (so-called markers) and an optimal access to operational areas.

This object is achieved by a device according to the features of claim 1. Advantageous embodiments are subject of the dependent claims.

The proposed device for attaching medical target devices, markers, probes or surgical instruments for image-guided, minimally invasive operations is characterized in that a support element which is preferably positioned with an adhesive layer on the body surface, has at least one positive retention for a fine-positioning unit that has a matching complementary shape. This enables a fixture in the manner of a snap closure, in particular to lock or clamp the fine-positioning unit quickly on the carrier element, so that a faster and more accurate structure is achieved. Also disassembling can be performed quickly after the performed operation. The positive retention is preferably glued or integrated to the shell or envelope of the support element (glued or poured into this). In particular this support has a hook shape with matching groove or complementary notch and/or a locking pin, so that the fine-positioning unit can be clicked or snapped quickly. Preferably, this complementary shape is integrated on the base plate of the fine-positioning unit, particularly at their cross slides in a robust manner.

Preferably the support member can be reversibly transferred from a stable dimension into a formable condition, in particular by releasing or applying vacuum in the carrier element. The fine-positioning unit preferably has two superposed cross slides, with which the fine adjustment of the tools, in particular needles, or the like can take place in the treatment, in particular by means of scaling. This can be performed on the fine-positioning unit by means of setting wheels which are preferably constructed with relatively large diameters, so that they protrude laterally over the compound slides. Thus, an easily accessible manual operation is possible. To facilitate fine positioning an optical sensor in the form of a laser pointer can be used to display the target point on the patient's skin.

The fine-positioning unit or their cross slides can be operated from a few meters distance via Bowden cables or adjusting spindles with flexible shafts or can be hydraulically/pneumatically operated remotely. Thus, the radiation exposure to the operator is considerably reduced. The holder and/or the carrier element can also be fixed via an adjusting arm to the treatment table, where in the application on the human back the holder is preferably plate-shaped, especially in T-shape. The mounting plate is particularly radiolucent and is preferably made of carbon in order to increase the stability of the device by the high stiffness of the material. To ensure a hygienic handling, several components of the device are preferably formed as sterile disposable articles. In addition, force sensors may be provided on the holder and/or fine positioning unit to detect breath or body movements, and to allow the feed of a puncture needle only in certain phases of movement.

Embodiments are described below with reference to the drawings. In the figures.

Figure 1:
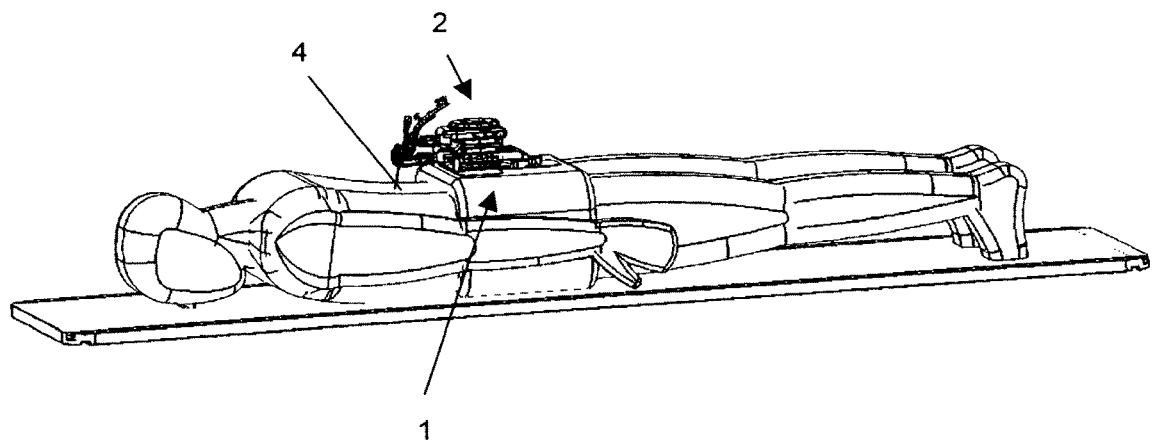
FIG. 1 is an overall view of the device on a patient.
Figure 4:
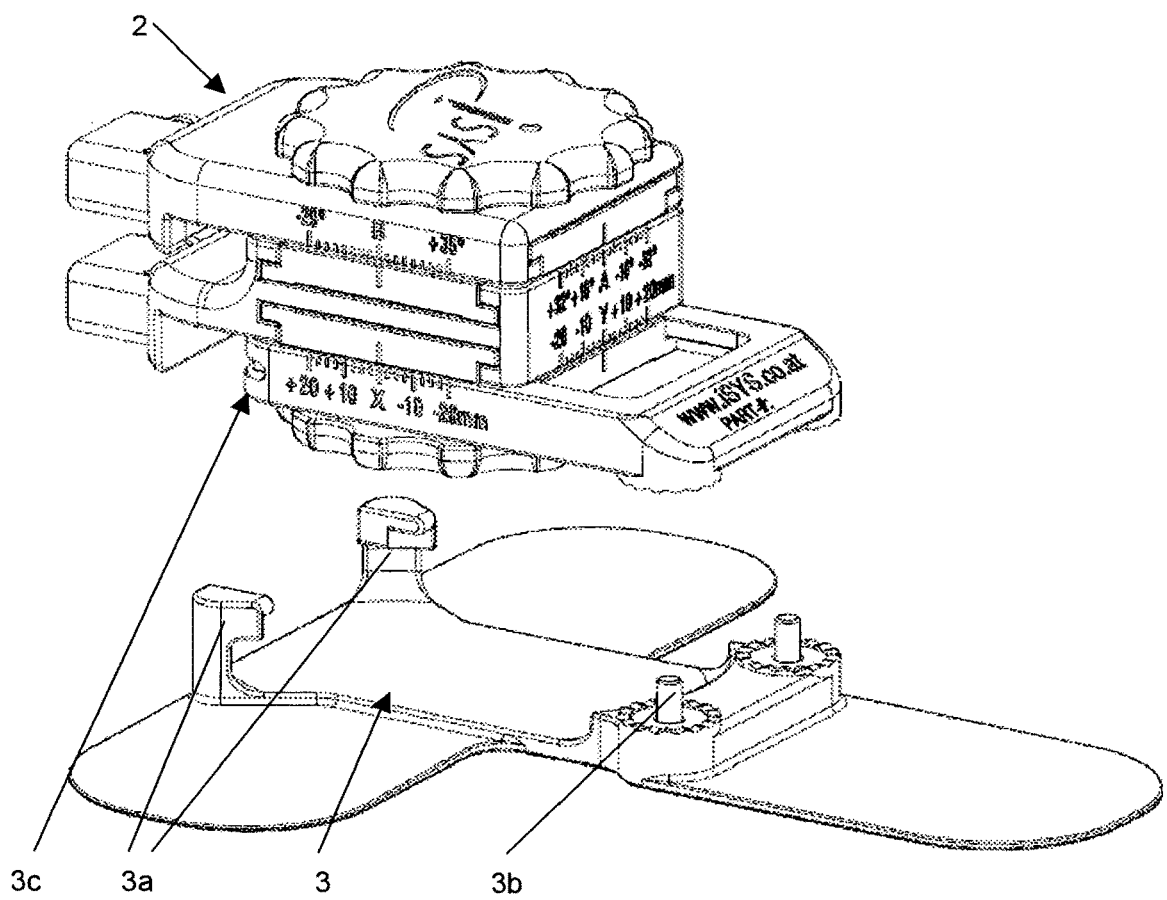
FIG. 4 is a fine-positioning unit shown above the holder.

FIG. 1 shows a proposed device at a patient on a treatment table. A carrier element 1 surrounds the back of the patient in a tunnel-like shape. This is preferably done by an adhesive layer, which is connected to the support element 1 and is pressed against the skin. The adhesive layer can also be formed by a spray adhesive, which is sprayed to the skin and/or the body-side surface of the carrier member 1. Then, a vacuum pump is preferably connected and the pad-like support 1 is evacuated. Thus, a dimensionally stable shell is formed on which a fine-positioning unit 2 is placed for adjusting a needle 4 by a bracket-like mount 3 (cf. especially FIG. 4). In this position, the support element 1 abuts with high gripping force at the back (or on the shoulders). Only after releasing the vacuum this support can be removed. Thus, the support member 1 can be reversed from the dimensionally stable fixing condition into a soft, formable state. Here, also a plurality of mutually independent vacuum chambers can be provided to partially destabilizing or stabilizing the device. Such vacuum chambers are known, f. i. from U.S. Pat. No. 7,881,823 B2, whose overall structure however is very bulky, while the proposed apparatus has a compact design.

Figure 2:
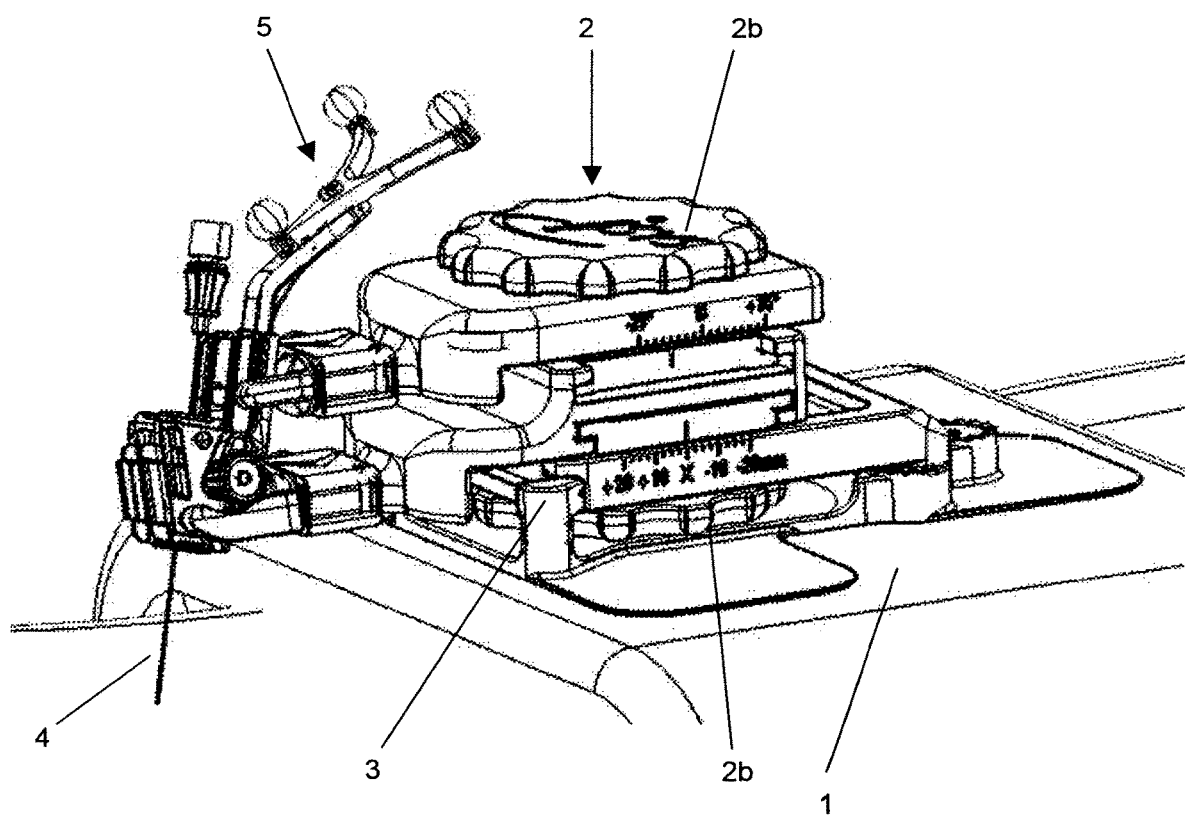
FIG. 2 is an enlarged perspective view of fine-positioning unit.

The shell of the support member 1 is preferably formed of fabric or film-like and is filled with granulate, in particular plastic beads. As shown in FIG. 2, the outer side of the solidified carrier element 1 has a plate-shaped support 3, preferably made of carbon (CFRP), which is attached thereto, in particular glued or mechanically fixed. For attachment to an operating table a swivel arm can also be provided. Further, FIG. 2 shows a three-armed marker 5 at the fine-positioning unit 2 above the puncture needle 4. In addition, the arrangement with two cross slides 2a (see also FIG. 5)

and the application of scales for manual adjustment is visible. Here, this fine adjustment is carried out via two large hand wheels 2b.

Figure 3:
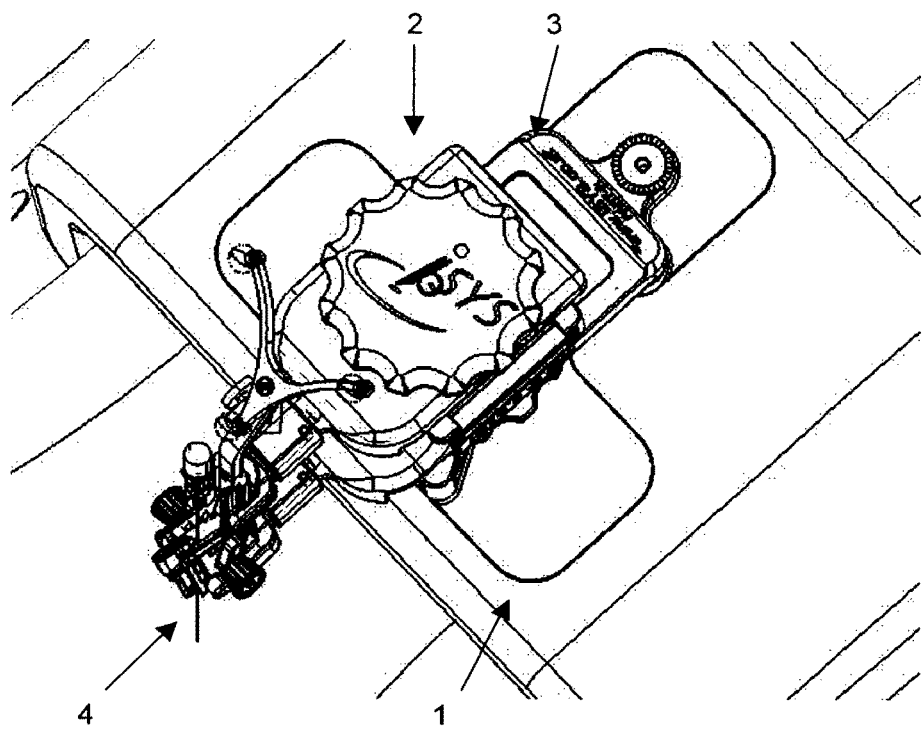
FIG. 3 is a plan view of the fine-positioning unit.

As shown in FIG. 3, the holder or mount 3 has a T-shape base on which the fine-positioning unit 2 is positively secured or locked. This is preferably done with hooks 3a, which are particularly visible in FIG. 4, left part. These hooks or projections engage into corresponding slots or complementary notches 3c at the fine-positioning unit 2, so that it is fixed down safely to the carrier element 1. For this purpose latching bolts 3b are also provided with which the fine-positioning unit 2 can be anchored securely and quickly. The removal or disassembling after treatment (e.g. rear marrow puncture in the lumbar region with the needle 4 navigating using the marker 5) can also be performed quickly, especially during treatment with sudden panic attacks of the patients.

Figure 5:
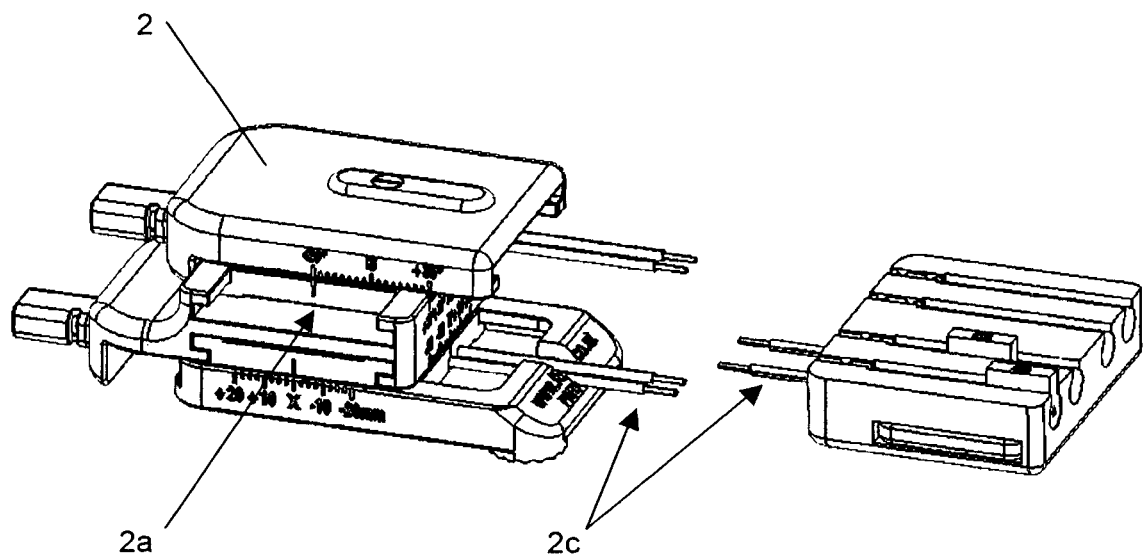
FIG. 5 is a fine-positioning unit with Bowden cables.
Figure 6:
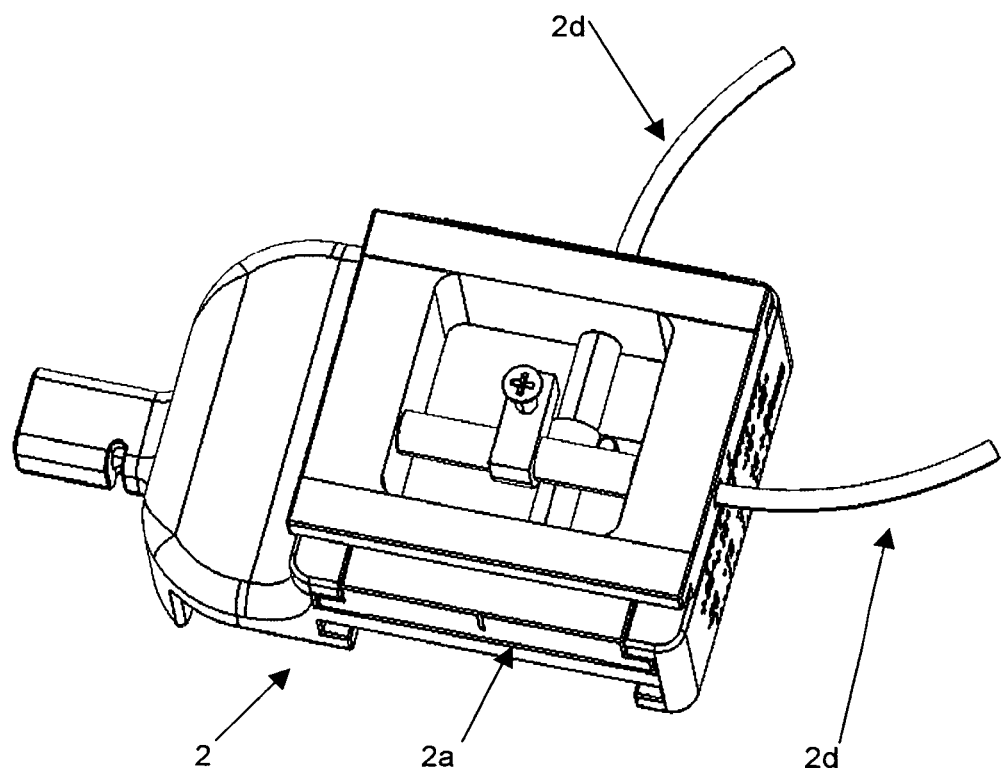
FIG. 6 is a fine-positioning unit with X/Y adjusting spindles.

In FIGS. 5 and 6 alternatives for adjusting the fine-positioning unit 2 are shown, namely in FIG. 5 with Bowden cables 2c and in FIG. 6 by means of adjusting spindles, which are remotely controlled via flexible shafts 2d. Here, the attending physician (or other professionals) can perform the X-Y displacement of the fine-positioning unit 2 from a distance of several meters. In addition to the scaling on the cross slides 2a displays or screens can also be provided. Equally hydraulic or pneumatic operations are feasible, wherein the components are preferably made metal-free. Thus, the device can be well used in the X-ray radiation or in the MR imaging. The control block for the Bowden cables 2c (in FIG. 5, right) does not have to be radiolucent or MR compatible, since these components are outside of the radiation field. In the case of hydraulic actuation (via hoses analogous to those flexible shafts 2d shown in FIG. 6) the hoses or cylinders can be filled with contrast agent. Thus, the volume in the cylinders can be monitored by 2D/3D image shots. From the volume in the cylinders the exact position of the X/Y stage can be determined. Besides the position calculation, the liquid in the cylinders can be used to register the needle position. The cylinder is hereby used as a kind of marker, with which target coordinates in the 2D/3D image data set can be calculated. Real-time imaging also enables a closed loop system by real-time calculation of cylinder volumes.

In this process the actual and target position (target point or cylinder volume) are adjusted as long as the values are within the predefined tolerance range. In addition, force sensors or optical sensors may also be provided at the fine-positioning unit 2 to control and monitor the treatment.

The drive systems described above can also be combined. Thus, mixed forms of manual and motorized units and subunits are possible (e.g. the semiautomatic driving to a target position). It is also conceivable that one or more slide planes commute freely to compensate f. i. collisions with patient/environment on active movement in a manner of an overload protection of one or more axes. Plural instruments can be provided at the fine-positioning unit 2 as well as marker/reference devices for (automatic) recognition by medical imaging and optical or magnetic measuring systems.

The invention claimed is:

1. A device for attachment of at least one of medical target devices, markers, probes and surgical instruments to a body surface of a patient for image-assisted, minimally invasive surgery, the device comprising:
   at least one carrier element that is configured to surround a back of the patient, the carrier element having a first surface that is configured to be positioned with an adhesive layer on the body surface of the patient, and the carrier element comprising at least one interlocking mount that is plate-shaped, the interlocking mount being attached to a second surface of the carrier element; and
   a fine-positioning unit comprising at least two superposed cross slides enabling to perform an X-Y-displacement of the fine-positioning unit for adjusting the at least one of medical target devices, markers, probes and surgical instruments with respect to the body surface of the patient,
   wherein the interlocking mount of the carrier element attaches to the fine-positioning unit, which has a matching complementary shape to that of the interlocking mount, and
   wherein the carrier element is configured to be modified from a dimensionally stable fixing condition to a soft, formable state and vice versa, by releasing or applying a vacuum to the carrier element, wherein, in the dimensionally stable fixing condition, the attachment of the carrier element to the patient occurs by at least vacuum.

2. A device according to claim 1, wherein the interlocking mount includes at least one of (i) a hook-shape and (ii) a latching pin.

3. A device according to claim 1, wherein the fine-positioning unit further comprises an overload safety device.

4. A device according to claim 1, wherein the fine-positioning unit is adjustable by means of adjusting wheels.

5. A device according to claim 1, wherein the fine-positioning unit is remotely controlled via one of Bowden cables or adjusting spindles, with at least one of flexible shafts and a hydraulic/pneumatic motor, in multiple axes.

6. A device according to claim 1, wherein the interlocking mount is T-shaped.

7. A device according to claim 1, wherein one or more components of the device are formed as a sterile disposable article.

8. A device according to claim 1, wherein the fine-positioning unit comprises scalings.

9. A device according to claim 1, wherein the fine-positioning unit comprises at least one of force sensors and optical sensors.

10. A device according to claim 1, wherein the interlocking mount is glued on an envelope of the carrier element.

11. A device according to claim 1, wherein the interlocking mount is glued to the second surface of the carrier element.

12. A device according to claim 1, wherein, in the dimensionally stable fixing condition, the attachment of the carrier element to the patient occurs by both vacuum and adhesion.

* * * * *